United States Patent
Castillo

[19]

[11] Patent Number: 5,881,729
[45] Date of Patent: Mar. 16, 1999

[54] WATER SPORTS EAR PLUG

[76] Inventor: Michael S. Castillo, 2138 Via Teca, San Clemente, Calif. 92673

[21] Appl. No.: 957,300

[22] Filed: Oct. 24, 1997

[51] Int. Cl.$^6$ ............................ A61F 11/00
[52] U.S. Cl. .................... 128/864; 128/867
[58] Field of Search ............ 128/846, 864–868; 2/2, 209; 181/129

[56] References Cited

U.S. PATENT DOCUMENTS

| | | | |
|---|---|---|---|
| 955,276 | 4/1910 | Lopizich | 128/866 |
| 2,070,403 | 2/1937 | Hershman | 128/864 |
| 4,537,187 | 8/1985 | Scott | 128/864 |
| 5,488,961 | 2/1996 | Adams | 128/864 |

*Primary Examiner*—Michael A. Brown
*Attorney, Agent, or Firm*—Stetina Brunda Garred & Brucker

[57] ABSTRACT

In accordance with the present invention, there is provided an ear plug for preventing water and wind from entering the ear canal while allowing audible tones to pass therethrough. The ear plug is provided with an ear plug housing which is provided with an outer member and an inner portion. The outer member is adapted to reside in the outer ear of the user and an elongate tubular member having an exterior portion adapted to extend downwardly within the ear canal of the user. The ear plug is further provided with an ear plug insert. The ear plug insert is provided with a retaining member which is generally annular, a membrane which is made of a water impervious material and is adapted to allow audible tones to pass therethrough, and an insert housing which is generally annular. The insert housing is provided with a first end which is axially disposable in the interior portion of the elongate tubular member which is adapted to receive the first end of the insert housing. The insert housing is further provided with a second end which is adapted to circumferentially receive the retaining member with the membrane securely disposed between thereto, so as to axially enclose the second end of the insert housing thereby preventing water and wind from entering the ear canal while allowing audible tones to pass therethrough.

8 Claims, 1 Drawing Sheet

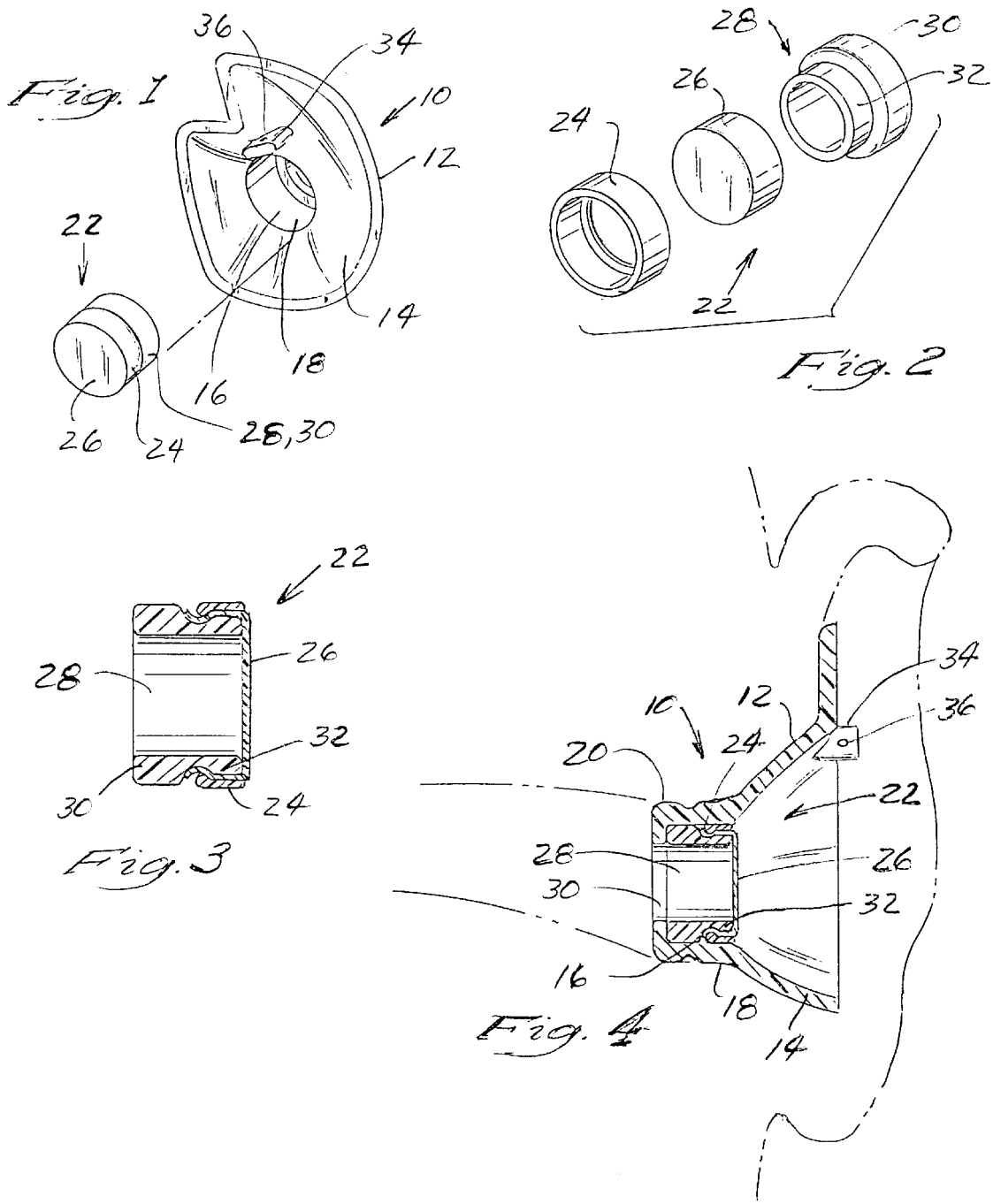

WATER SPORTS EAR PLUG

FIELD OF THE INVENTION

The present invention relates generally to an ear plug, and more particularly to an ear plug which prevents water and wind from entering the ear canal while permitting audible sounds to pass therethrough.

BACKGROUND OF THE INVENTION

Surfers, swimmers, water skiers, and others who are in substantial contact with water often encounter problems with water entering the ear canal. This is particularly troublesome when the water entering the ear canal is relatively cold or becomes cold as a result of wind. A person subject to repeated conditions of this nature may develop a condition commonly referred to as surfer's ear (the development of bony stenosis of the external auditory canal due to diffuse exostoses).

The present invention relates to an improved ear plug. While simply plugging the ear canal may serve to prevent water and wind from entering the ear canal, the ability to hear audible tones may be substantially impaired. Previous efforts to keep water out without impairing the user's ability to hear have employed ear plugs with small openings to the ear canal. While such openings may impair the passage of water and wind, such a configuration, nonetheless, allows for the passage of undesired water and wind. Accordingly, there is a need in the art for a device which prevents water and wind from entering the ear canal while allowing audible tones to pass.

SUMMARY OF THE INVENTION

In accordance with the present invention, there is provided an ear plug for preventing water and wind from entering the ear canal while allowing audible tones to pass therethrough. The ear plug is provided with an ear plug housing which is provided with an outer member and an inner portion. The outer member is adapted to reside in the outer ear of the user and an elongate tubular member having an exterior portion adapted to extend downwardly within the ear canal of the user. The ear plug is further provided with an ear plug insert. The ear plug insert is provided with a retaining member which is generally annular, a membrane which is made of a water impervious material and is adapted to allow audible tones to pass therethrough, and an insert housing which is generally annular. The insert housing is provided with a first end which is axially disposable in the interior portion of the elongate tubular member which is adapted to receive the first end of the insert housing. The insert housing is further provided with a second end which is adapted to circumferentially receive the retaining member with the membrane securely disposed between thereto, so as to axially enclose the second end of the insert housing thereby preventing water and wind from entering the ear canal while allowing audible tones to pass therethrough.

In the preferred embodiment of the present invention, the ear plug housing is further provided with a tabbed member having a hole. The hole is used for receiving a leash. In addition, the membrane may be constructed of a polymer material and may be further adapted to amplify audible tones as such audible tones pass through the membrane at the second end toward the second end and into the ear canal.

Further in accordance with the present invention, there is provided an ear plug insert disposable in an ear plug housing for preventing water and wind from entering the ear canal while allowing audible tones to pass therethrough. The ear plug housing is provided with an outer member and an inner portion. The outer member is adapted to reside in the outer ear of the user and an elongate tubular member having an exterior portion adapted to extend downwardly within the ear canal of the user. The ear plug insert is provided with a retaining member which is generally annular, a membrane which is made of a water impervious material and is adapted to allow audible tones to pass therethrough, and an insert housing which is generally annular. The insert housing is provided with a first end which is axially disposable in the interior portion of the elongate tubular member which is adapted to receive the first end of the insert housing. The insert housing is further provided with a second end which is adapted to circumferentially receive the retaining member with the membrane securely disposed between thereto, so as to axially enclose the second end of the insert housing thereby preventing water and wind from entering the ear canal while allowing audible tones to pass therethrough.

In another embodiment of the present invention, there is provided a method of retrofitting an ear plug housing for preventing water and wind from entering the ear canal while allowing audible tones to pass therethrough. The method has application to an ear plug housing which is provided with an outer member, adapted to reside in the outer ear of the user and an elongate tubular member having an exterior portion adapted to extend downwardly within the ear canal of the user, and an interior portion. The method begins with the initial step of forming a retaining member being generally annular. Next, the method calls for forming a membrane being made of a water impervious material and adapted to allow audible tones to pass therethrough. The method next calls for forming an insert housing being generally annular and having a first end and a second end adapted to circumferentially receive the retaining member with the membrane securely disposed between thereto. The membrane is then secured at the second end with the retaining member so as to axially enclose the second end of the insert housing thereby preventing water and wind from entering the insert housing while allowing audible tones to pass therethrough. The interior portion of the elongate tubular member of the ear plug housing is next adapted to receive the first end of the insert housing so as prevent water and wind from passing between the interior portion and the first end. Finally the insert housing is axially disposed into the interior portion of the elongate tubular member of the ear plug housing thereby preventing water and wind from entering the ear canal while allowing audible tones to pass therethrough.

The present invention addresses the various problems associated with the prevention of water and wind entering the ear canal while allowing audible tones to pass. The use of the membrane achieves the goal of preventing water and wind to enter the ear canal. Advantageously, the ear plug insert defines a pocket of dead air space in the ear canal which acts as an effective insulator against temperature changes. Further, the ear plug insert with the membrane securely disposed about one of its ends is similar in configuration to a drum. This allows for the membrane to vibrate thereby allowing audible tones to pass. The diameter of the ear plug insert and the material selection and thickness of the membrane may be optimized with regard to sound wave lengths so as to amplify specific audible tones.

An additional attribute of the present invention is that the membrane is readily removable. This allows for easy maintenance and cleaning (as may be necessary to wash off salt deposits after surfing in the ocean). In addition, other ear plug designs may require entire ear plug replacement when the ear plug loses its effectiveness. In the case of the present invention, however, the easy removal of the membrane allows for convenient replacement of the membrane only. Furthermore, the replacement cost of the membrane is inexpensive in relation to replacement of the entire ear plug device.

In addition, an ear plug insert constructed in accordance with the present invention may be disposable into an existing ear plug housing. Such an ear plug 'retrofit' allows for the low cost salvage of an existing ear plug housing, as may be desired in the case of an ear plug housing customized to the contours of the user's outer ear and ear canal.

BRIEF DESCRIPTION OF THE DRAWINGS

These, as well as other features of the present invention, will become more apparent upon reference to the drawings wherein:

FIG. 1 is a perspective view of an ear plug constructed in accordance with the present invention;

FIG. 2 is a perspective view of an ear plug insert constructed in accordance with the present invention;

FIG. 3 is a cross-sectional view of an ear plug insert constructed in accordance with the present invention; and FIG. 4 is a cross-sectional view of an ear plug constructed in accordance with the present invention.

DETAILED DESCRIPTION OF THE PREFERRED EMBODIMENT

Referring now to the drawing wherein the showings are for purposes of illustrating of a preferred embodiment of the present invention only, and not for purposes of limiting the same, FIGS. 1–4 illustrate an ear plug 10 constructed in accordance with the present invention. As will be described in more detail below, the ear plug 10 is designed to prevent water and wind from entering the ear canal while allowing audible tones to pass.

Referring now to FIGS. 1–4, in accordance with the present invention, there is provided an ear plug 10 for preventing water and wind from entering the ear canal while allowing audible tones to pass therethrough. The ear plug 10 is provided with an ear plug housing 12 which is provided with an outer member 14 and an inner portion 16. The outer member 14 is adapted to reside in the outer ear of the user and an elongate tubular member 18 having an exterior portion 20 adapted to extend downwardly within the ear canal of the user. The ear plug 10 is further provided with an ear plug insert 22. The ear plug insert 22 is provided with a retaining member 24 which is generally annular, a membrane 26 which is made of a water impervious material and is adapted to allow audible tones to pass therethrough, and an insert housing 28 which is generally annular. The insert housing 28 is provided with a first end 30 which is axially disposable in the interior portion 16 of the elongate tubular member 18 which is adapted to receive the first end 30 of the insert housing 28. The insert housing 28 is further provided with a second end 32 which is adapted to circumferentially receive the retaining member 24 with the membrane 26 securely disposed between thereto, so as to axially enclose the second end 32 of the insert housing 28 thereby preventing water and wind from entering the ear canal while allowing audible tones to pass therethrough.

In the preferred embodiment of the present invention, the ear plug housing 12 is further provided with a tabbed member 34 having a hole 36. The hole 36 is used for receiving a leash (not depicted). In addition, the membrane 26 may be constructed of a polymer material and may be further adapted to amplify audible tones as such audible tones pass through the membrane 26 at the first end 30 toward the second end 32 and into the ear canal. It is contemplated that the membrane 26 may be constructed of more than one layer of material. It is contemplated that the membrane 26 would be constructed of a material well known to those skilled in the art. It is contemplated that the diameter of the insert housing 28 at the first end 30 and second end 32 will be sized and configured so as to amplify specific audible tonal ranges. It is contemplated that the diameter at the first end 30 and at the second end 32 may be different. The sizing of the of the first end 30 and the second end 32 are well known to those skilled in the art. In addition, it is contemplated that the sound amplification may be a function of the axial length of the insert housing 28.

It is contemplated that the material selection for the ear plug housing 12 will be constructed of a material which is light weight and flexible so as to be comfortable for the user. In addition it is contemplated that the ear plug 10 will have an overall density of less than 1 whereby the ear plug 10 will float in water. It is contemplated that the ear plug 10 and its component parts may be constructed of a material having various colorations and patterns, is as to be readily visible if it should become unattached from the user. It is further contemplated that the ear plug 10 and its component parts may be constructed of semi-transparent material so as to conceal the user's usage of the ear plug 10. The above described materials are those which are well known to those skilled in the art.

Additional modification and improvements of the present invention may also be apparent to those of ordinary skill in the art. Thus, the particular combination of parts described and illustrated herein is intended to represent only one embodiment of the present invention, and is not intended to serve as limitation of alternative devices within the spirit and scope of the invention.

What is claimed is:

1. An ear plug for preventing water and wind from entering the ear canal while allowing audible tones to pass therethrough comprising:

an ear plug housing comprising an outer member adapted to reside in the outer ear of the user and an elongate tubular member having an exterior portion adapted to extend downwardly within the ear canal of the user and an interior portion; and an ear plug insert comprising:
  (i) a retaining member being generally annular and axially engagable in slidable communication with the interior portion of the elongate tubular member;
  (ii) a membrane being made of a water impervious material and adapted to allow audible tones to pass therethrough; and
  (iii) an insert housing being generally annular, having a first end axially disposable in the interior portion of the elongate tubular member adapted to receive the first end of the insert housing, and a second end adapted to circumferentially receive the retaining member with the membrane securely disposed between thereto, so as to axially enclose the second end of the insert housing thereby preventing water and wind from passing through the insert housing and passing between the interior portion of the tubular member and the retaining member and entering the ear canal while allowing audible tones to pass therethrough.

2. An ear plug of claim 1 wherein the ear plug housing further comprising a tabbed member having a hole for receiving a leash.

3. An ear plug of claim 1 wherein the membrane being made of a polymer material.

4. An ear plug of claim 1 wherein the membrane is further adapted to amplify audible tones as such audible tones pass through the membrane at the second end toward the second end and into the ear canal.

5. An ear plug insert, disposable in an ear plug housing having an elongate tubular member having an exterior portion adapted to extend downwardly within the ear canal of the user and an interior portion, for preventing water and wind from entering the ear canal while allowing audible tones to pass therethrough comprising:

a retaining member being generally annular and axially engagable in slidable communication with the interior portion of the elongate tubular member;

a membrane being made of a water impervious material and adapted to allow audible tones to pass therethrough; and an insert housing being generally annular, having a first end axially disposable in the interior portion of the elongate tubular member adapted to receive the first end of the insert housing, and a second end adapted to circumferentially receive the retaining member with the membrane securely disposed between thereto, so as to axially enclose the second end of the insert housing thereby preventing water and wind from passing through the insert housing and passing between the interior portion of the tubular member and the retaining member and entering the ear canal while allowing audible tones to pass therethrough.

6. An ear plug insert of claim 5 wherein the membrane being made of a polymer material.

7. An ear plug insert of claim 5 wherein the membrane is further adapted to amplify audible tones as such audible tones pass through the membrane at the second end toward the second end and into the ear canal.

8. A method of retrofitting an ear plug housing, including an outer member adapted to reside in the outer ear of the user and an elongate tubular member having an exterior portion adapted to extend downwardly within the ear canal of the user and an interior portion, for preventing water and wind from entering the ear canal while allowing audible tones to pass therethrough comprising the following steps:

(a) forming a retaining member being generally annular and axially engagable in slidable communication with the interior portion of the elongate tubular member;

(b) forming a membrane being made of a water impervious material and adapted to allow audible tones to pass therethrough;

(c) forming an insert housing being generally annular and having a first end and a second end adapted to circumferentially receive the retaining member with the membrane securely disposed between thereto;

(d) securing the membrane at the second end with the retaining member so as to axially enclose the second end of the insert housing thereby preventing water and wind from entering the insert housing while allowing audible tones to pass therethrough;

(e) adapting the interior portion of the elongate tubular member of the ear plug housing to receive the first end of the insert housing and the retaining member so as prevent water and wind from passing between the interior portion and the first end and between the interior portion and the retaining member; and (f) axially disposing the insert housing into the interior portion of the elongate tubular member of the ear plug housing thereby preventing water and wind from passing through the insert housing and passing between the interior portion of the tubular member and the retaining member and entering the ear canal while allowing audible tones to pass therethrough.

* * * * *